United States Patent
Wagner et al.

(10) Patent No.: US 7,142,912 B2
(45) Date of Patent: Nov. 28, 2006

(54) METHOD AND APPARATUS FOR ASSESSING AND TREATING ATRIAL FIBRILLATION RISK

(75) Inventors: Darrell O. Wagner, Isanti, MN (US); Robert J. Sweeney, Woodbury, MN (US); Adam W. Cates, Minneapolis, MN (US); Apurv Kamath, Minneapolis, MN (US); Eric G. Lovett, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 632 days.

(21) Appl. No.: 10/194,435

(22) Filed: Jul. 12, 2002

(65) Prior Publication Data

US 2004/0010291 A1 Jan. 15, 2004

(51) Int. Cl.
*A61N 1/08* (2006.01)
(52) U.S. Cl. .......................... 607/4; 600/518
(58) Field of Classification Search ............... 600/515, 600/518, 519; 607/4, 5, 9, 14
See application file for complete search history.

(56) References Cited

U.S. PATENT DOCUMENTS

| 5,190,035 | A |   | 3/1993  | Salo et al. |           |
|-----------|---|---|---------|-------------|-----------|
| 5,330,508 | A | * | 7/1994  | Gunderson   | 607/14    |
| 5,730,141 | A | * | 3/1998  | Fain et al. | 600/518   |
| 5,788,645 | A | * | 8/1998  | Swanson et al. | 600/516 |
| 5,891,170 | A | * | 4/1999  | Nitzsche et al. | 607/4 |
| 6,161,042 | A |   | 12/2000 | Hartley et al. |        |
| 6,292,695 | B1 | * | 9/2001 | Webster, Jr. et al. | 607/14 |

OTHER PUBLICATIONS

Hasdemir, C., "Endovascular Stimulation of Autonomic Neural Elements in the Superior Vena Cava Using a Flexible Loop Catheter", *Pacing and Clinical Electrophysiology, v. 24, Part II*, (Apr. 2000), 691.

Schauerte, Patrick N., "Transvenous Parasympathetic Nerve Stimulation in the Inferior Vena Cava and Atrioventricular Conduction", *Journal of Cardiovascular Electrophysiology, 11(1)*, (Jan. 2000), 64-69.

Scherlag, M. A., "Endovascular Neural Stimulation Via a Novel Basket Electrode Catheter: Comparison of Electrode Configurations", *Journal of Interventional Cardiac Electrophysiology, 4(1)*, (Apr. 2000), 219-224.

Zhang, Youhua, et al., "Cardiac performance is improved during atrial fibrillation by discrete nerve stimulation", *PACE, 24(4)(II), Abstract 228* (2001), 1 page.

* cited by examiner

*Primary Examiner*—George R. Evanisko
*Assistant Examiner*—Michael Kahelin
(74) *Attorney, Agent, or Firm*—Schwegman, Lundberg, Woessner, & Kluth, P.A.

(57) ABSTRACT

A method and apparatus for assessing the risk of atrial fibrillation in a patient by calculating the relative frequency of short and long intervals between successive heart beats during sinus rhythm is presented. An imbalance of short over long sinus intervals has been found to indicate a higher risk of atrial fibrillation. An implantable cardiac device may be configured to automatically deliver interventional therapy to restore sinus interval balance when such an imbalance is detected.

22 Claims, 4 Drawing Sheets

METHOD AND APPARATUS FOR ASSESSING AND TREATING ATRIAL FIBRILLATION RISK

FIELD OF THE INVENTION

This invention pertains to systems and methods for cardiac rhythm management. In particular, the invention relates to the diagnosis and treatment of atrial fibrillation.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include sinus tachycardia, ventricular tachycardia, ventricular fibrillation (VF), atrial tachycardia, and atrial fibrillation (AF). Tachycardia is characterized by a rapid rate, either due to an ectopic excitatory focus or abnormal excitation by normal pacemaker tissue, while fibrillation occurs when the chamber depolarizes in a chaotic fashion with abnormal depolarization waveforms as reflected by an EKG.

An electrical shock applied to a heart chamber (i.e., defibrillation or cardioversion) can be used to terminate most tachyarrhythmias by depolarizing excitable myocardium, which thereby prolongs refractoriness, interrupts reentrant circuits, and discharges excitatory foci. Implantable cardioverter/defibrillators (ICDs) provide this kind of therapy by delivering a shock pulse to the heart when fibrillation is detected by the device. ICDs can be designed to treat either atrial or ventricular tachyarrhythmias, or both, and may also incorporate cardiac pacing functionality. The most dangerous tachyarrhythmias are ventricular tachycardia and ventricular fibrillation, and ICDs have most commonly been applied in the treatment of those conditions.

ICDs are also capable, however, of detecting atrial tachyarrhythmias, such as atrial fibrillation and atrial flutter, and delivering a shock pulse to the atria in order to terminate the arrhythmia. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy.

No matter what treatment modality is used, it would be beneficial if there were a technique by which the risk of atrial fibrillation could be assessed at any particular time. A convenient way of assessing atrial fibrillation risk would be useful both in screening patients and as an aid to treatment planning. Such a technique could also be used by implantable or external devices in delivering therapy or in performing a monitoring function.

SUMMARY

In accordance with the invention, the risk for atrial fibrillation can be assessed by determining the relative frequency of short and long time intervals between successive heart beats during sinus rhythm. It has been observed that patients who are at increased risk for atrial fibrillation exhibit a greater frequency of short sinus intervals relative to long sinus intervals. In a particular embodiment, an implantable cardiac rhythm management device is programmed to assess a patient's risk for atrial fibrillation from interval data acquired through the device's sensing channels. External monitoring or therapeutic devices may also be configured to acquire heart beat intervals by electrocardiographic or other means and assess atrial fibrillation risk. Such information may be communicated to a clinician to assist in diagnosis and treatment decisions or used by the device to trigger more computationally intensive analysis. The device may be further configured to automatically initiate therapy to restore balance to the sinus intervals when an increased risk for atrial fibrillation is detected.

DETAILED DESCRIPTION

When intervals between successive heart beats during sinus rhythm, referred to as sinus intervals, are measured, these intervals can be considered to exhibit a certain variability about an average or mean interval value. It has been found that in patients who are not prone to atrial fibrillation, shorter than average sinus intervals and longer than average sinus intervals occur with equal probability. In patients at increased risk for developing atrial fibrillation, on the other hand, shorter than average sinus intervals occur at a greater frequency than longer than average sinus intervals. The present invention provides a procedure by which patients who are at risk for experiencing episodes of atrial fibrillation can be identified and/or by which the risk of atrial fibrillation occurring at a certain time can be assessed. In accordance with the procedure, each measured sinus interval is classified as either normal, short, or long by comparing the interval with a moving short-term average of previous sinus intervals according to a specified criterion. The frequency of occurrence of short sinus intervals can then be compared with the frequency of occurrence of long sinus intervals over a specified period of time. If the short sinus interval frequency is greater than the long sinus interval frequency and also greater than a specified threshold value, a greater risk for the occurrence of atrial fibrillation is determined to be present.

One way of implementing the method described above for assessing the risk of atrial fibrillation in a patient is for a clinician to measure sinus intervals over some period of time using external monitoring equipment. In the alternative, and as described more fully below, an implantable cardiac rhythm management device (e.g., an ICD, pacemaker, or combination device) or an externally mounted monitoring device may be programmed to collect interval data from its sensing channels either continuously or at periodic intervals. The computations for determining an increased risk for atrial fibrillation could then be performed by the device with the results downloaded to an external programmer. Alternatively, the external programmer could perform the computations based upon the sinus interval data downloaded to it. In any case, the clinician may then make appropriate diagnostic and treatment decisions based upon the collected data. An implantable cardiac rhythm management device may also be configured and programmed to automatically deliver a preventive therapy that decreases a patient's risk for atrial fibrillation by restoring balance to the sinus intervals when an imbalance indicating an increased risk is detected.

1. Hardware Platforms

The present invention may be incorporated into either an externally mounted cardiac device or an implantable cardiac rhythm management device such as an ICD or pacemaker. Examples of such devices are illustrated in FIGS. 1A and 1B as described below.

Figure 1A:
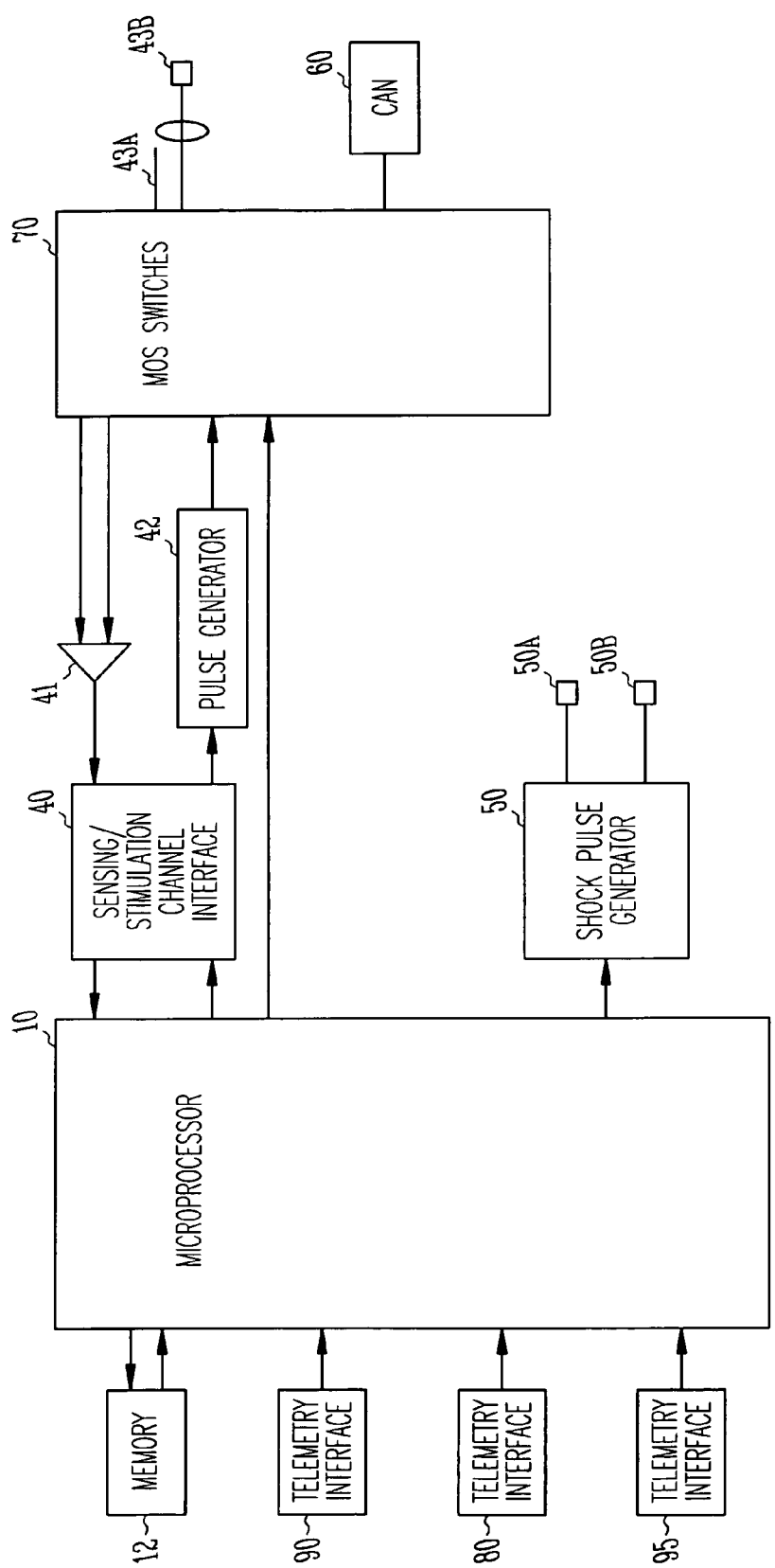
FIG. 1A is a system diagram of an exemplary implantable cardiac rhythm management device.
Figure 1B:
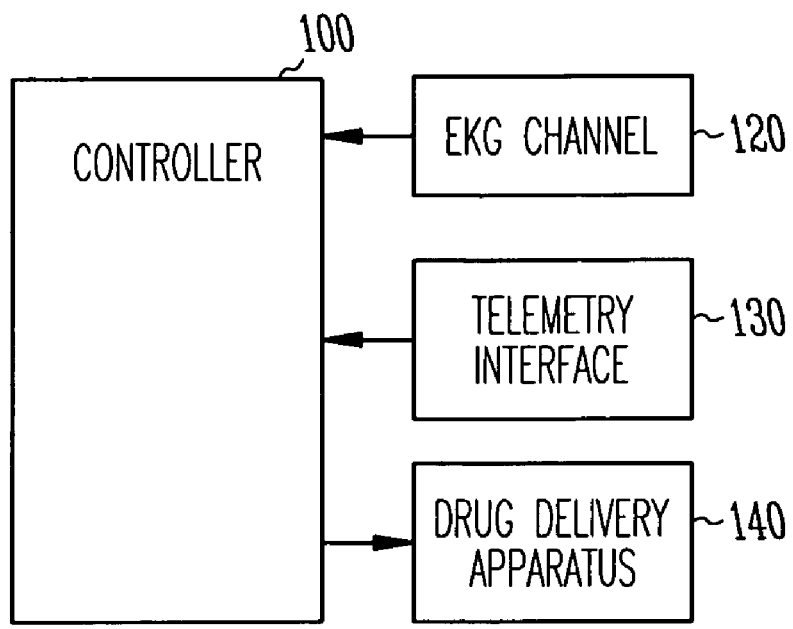
FIG. 1B is a system diagram of an external cardiac monitoring device.

A block diagram of an exemplary cardiac rhythm management device is shown in FIG. 1A. Cardiac rhythm management devices are typically implanted subcutaneously on a patient's chest and have leads threaded intravenously into the heart to connect the device to electrodes used for sensing and delivery of pacing pulses or defibrillation shocks. A programmable electronic controller causes defibrillation shocks to be delivered when an arrhythmia is detected, and also controls the output of pacing pulses in the case of a device with pacemaker functionality. The controller of the device is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The device has one or more sensing/stimulation channels, where a sensing channel is used for sensing cardiac electrical activity and a stimulation channel is used for delivering pacing or other types of stimulation pulses. A device may have multiple channels such as an atrial sensing/stimulation channel and a ventricular sensing/stimulation channel for sensing and pacing both heart chambers. For illustrative purposes, FIG. 1A shows an exemplary sensing/stimulation channel which utilizes a single lead connected to the device which includes a ring electrode 43a and tip electrode 43b for bipolar sensing and stimulation. In a device with a pacemaker functionality, the sensing channel is used to sense intrinsic cardiac activity, while the stimulation channel is used for delivering paces to the heart in accordance with a pacing algorithm. A sensing channel may also be used to count beats in the sensed chamber in order to detect arrhythmias. A MOS switching network 70 controlled by the microprocessor is used to switch the electrodes to the input of a sense amplifier 41 for the sensing channel or to the output of a pulse generator 42 for the stimulation channel. The switching network may also be used to connect only one of either the ring or tip electrode to the pulse generator 42 or sensing amplifier 41 for unipolar sensing or stimulation, in which case the conductive case of the device or can 60 is used as the other electrode. A sensing channel may also use the shock leads rather than the sensing leads for detecting atrial or ventricular beats.

The channel interface 40 communicates bidirectionally with a port of microprocessor 10 and may include an analog-to-digital converter for digitizing sensing signal inputs from the sensing amplifier, registers that can be written to for adjusting the gain and threshold values of the sensing amplifier, and registers for controlling the output of stimulation pulses and/or changing the stimulation pulse amplitude or frequency. A defibrillation shock pulse generator 50 with shock leads 50a and 50b for delivering cardioversion/defibrillation shocks to the atria is also interfaced to the controller. Also provided is a telemetry interface 95 for communicating with an external programmer.

Also provided in this embodiment are an accelerometer 80 and an impedance measuring circuit 90 that can be used to determine the patient's exertion level for rate-adaptive pacing by measuring activity level and minute ventilation, respectively. The accelerometer and impedance measuring circuit can also be used to detect ventricular contractions by sensing heart sounds and variations in cardiac stroke volume, respectively. (See, e.g., U.S. Pat. Nos. 5,190,035 and 6,161,042, assigned to the assignee of the present invention and hereby incorporated by reference.) The controller 10 controls the overall operation of the device in accordance with programmed instructions stored in memory, including controlling the delivery of stimulation pulses, interpreting sense signals received from the sensing channels, and implementing timers that may be used for various purposes. The sensing circuitry of the pacemaker detects a chamber sense when an electrogram signal (i.e., a voltage sensed by an electrode representing cardiac electrical activity) generated by a particular channel exceeds a specified detection threshold. A chamber sense may be either an atrial sense or a ventricular sense depending on whether it occurs in the atrial or ventricular sensing channel. Pacing algorithms used in particular pacing modes employ such senses to trigger or inhibit pacing. By measuring the interval between successive atrial and ventricular senses, the controller is also able to measure atrial and ventricular rates and detect arrhythmias in those chambers using rate-based criteria. As described below, the controller may also be programmed to collect and analyze intervals between successive atrial or ventricular senses (i.e., PP and RR intervals, respectively, referring to a surface EKG waveform) during sinus rhythm to assess the patient's atrial fibrillation risk. Sinus intervals may also be computed by detecting successive heart beats from impedance changes due to cardiac blood flow with the impedance measuring circuitry 90 or from heart sounds with the accelerometer 80. If a sinus interval imbalance is detected, the device may additionally be configured to deliver interventional therapy of some kind in order to restore balance to the intervals.

FIG. 1B shows a block diagram of an exemplary external cardiac monitoring device that includes a controller 100 and an EKG sensing channel 120. The EKG sensing channel would include surface electrodes for placement on a patient's body and appropriate amplification and filtering circuitry. As with the implantable device described above, the controller is programmed to collect sinus interval data from the EKG sensing channel and assess the patient's atrial fibrillation risk. If an increased risk is detected, an alarm function may be incorporated into the device to warn the patient so that appropriate action may be taken. Alarms and other information may also be communicated to an external device via a telemetry interface 130. The controller may be further programmed to deliver a drug in response to an increased atrial fibrillation risk by issuing a command to a drug delivery apparatus 140.

2. Risk Assessment Algorithm

In order to assess the risk of atrial fibrillation, the relative frequencies of short sinus intervals and long sinus intervals are determined and compared. As each sinus interval is measured, the current sinus interval is divided by the short-term average sinus interval to compute an interval ratio for each measured sinus interval. The short-term average sinus interval is computed as a moving average of a specified number of sinus intervals. Interval ratios are computed and collected for a specified period of time. Interval ratios within a first specified range less than one are classified as short interval ratios, while interval ratios within a specified range greater than one are classified as long interval ratios. The number of short and long interval ratios are then counted and an occurrence frequency for each type of interval ratio is determined by dividing the count by the total number of interval ratios collected. If the short interval ratio frequency is greater than the long interval ratio frequency and also greater than a specified threshold value, an increased probability for the occurrence of atrial fibrillation is determined.

In order to measure the sinus rate and determine the relative frequencies of short and long sinus intervals, heart beats can be detected during sinus rhythm as atrial or ventricular senses from an electrogram or surface EKG. An appropriately equipped device such as that in FIG. 1A may also detect successive heart beats by other means such as sensing heart sounds with the accelerometer 80 or sensing stroke volume with the impedance measurement circuitry 90. In the exemplary embodiment to be described, sinus intervals are measured as the intervals between ventricular beats (i.e., RR intervals) during sinus rhythm as detected from a surface EKG waveform or electrograms generated in a sensing channel configured to sense ventricular activity. It should be appreciated, however, that the algorithm could equally as well be applied to other measures of sinus rate.

Figure 2:
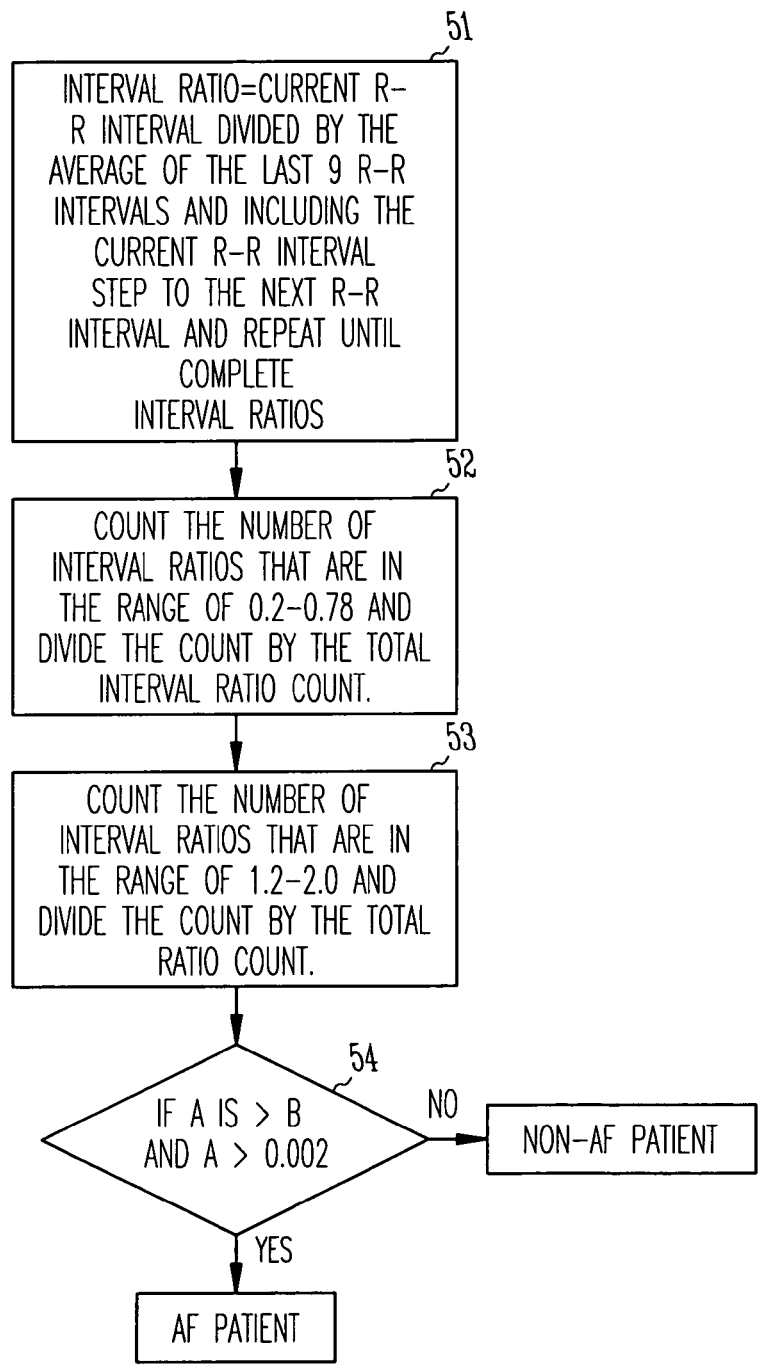
FIG. 2 illustrates an exemplary algorithm for determining atrial fibrillation risk.

FIG. 2 illustrates a particular example of the algorithm as it could be implemented in the controller's programming using specific range and threshold values. The interval ratio is defined here as the current RR interval divided by the average of the last nine RR intervals and the current RR interval. At step S1, RR intervals are measured and interval ratios are computed for a specified period of time (e.g., 30 minutes). At step S2, the number of computed interval ratios that are in the range between 0.2 and 0.78 are counted and divided by the total number of interval ratios. This is the short interval frequency A. The long interval frequency B is calculated at step S3 by counting the number of computed interval ratios that are in the range between 1.2 and 2.0 and dividing by the total number of interval ratios. At step S4, the risk of atrial fibrillation is assessed as high if the short interval frequency A is greater than the long interval ratio B and greater than a specified threshold value of 0.002. Otherwise, the risk of atrial fibrillation is determined to be low.

When a risk assessment as performed above indicates that the patient is at increased risk for atrial fibrillation, such information may be downloaded to an external programmer to aid a clinician in deciding how to best treat the patient. The device may also be capable of performing other types of computationally intensive data analysis for predicting when atrial fibrillation is likely to occur that may be triggered when the sinus interval data indicates an increased risk is present, including analysis of electrogram waveform morphology. Such analysis may involve, for example, cross-correlation of electrogram waveforms with template waveforms representing an arrhythmogenic situation. As described below, the device may also be configured to deliver therapy to restore balance to the sinus intervals and decrease the risk for atrial fibrillation.

3. Intervention Methods

For patients identified as having a greater incidence of short sinus intervals than long sinus intervals, the sinus interval balance may be restored by delivering a therapy that has the effect of increasing the frequency of long sinus intervals and/or decreasing the frequency of short sinus intervals. The therapy may affect the intervals between atrial contractions (PP intervals), ventricular contractions (RR intervals), or both. Such sinus interval rebalancing therapy may be delivered periodically, at random times, or in response to a currently measured short sinus interval.

Figure 3:
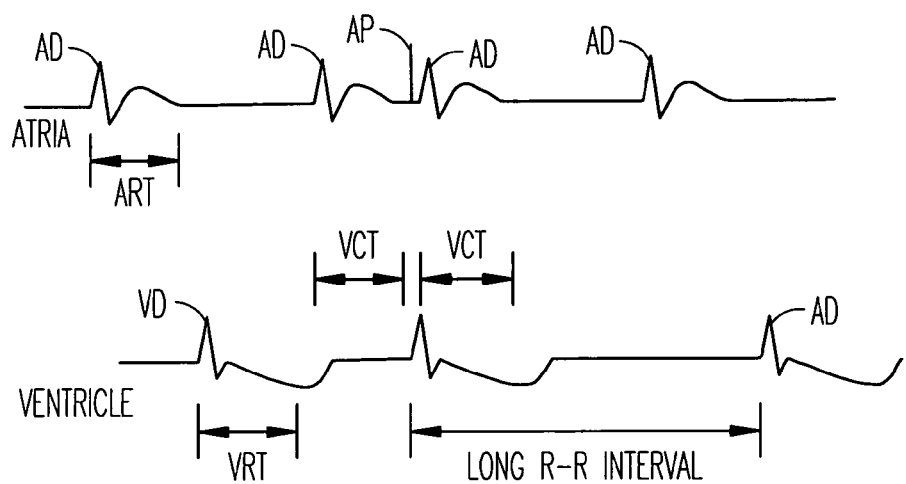
FIG. 3 depicts electrogram waveforms of the atria and ventricles when pacing the atria to lengthen the sinus interval.

In one embodiment, RR intervals are lengthened by pacing the atria while the ventricles are refractory. If the ventricular refractory period is longer than the normal AV conduction time, the ventricles do not respond to the conducted atrial depolarization. The next ventricular contraction then does not occur until the next atrial depolarization, thus lengthening the RR interval. FIG. 3 illustrates this approach where an atrial electrogram and a ventricular electrogram are shown. Each atrial depolarization AD is followed after a ventricular conduction time VCT by a ventricular depolarization VD. The ventricular conduction time is the time required for excitation from the atria to traverse the specialized AV conduction system and excite the ventricles. After an atrial depolarization, the atria are refractory to further stimulation for an atrial refractory time ART, and the ventricles are similarly refractory for a ventricular refractory time VRT following a ventricular depolarization. In order to lengthen the RR interval, an atrial pace AP is delivered after the atrial refractory period ART so as to cause an atrial depolarization but early enough so that the ventricles are still refractory when the excitation from the atria arrives after the ventricular conduction time. The result is a resetting of the intrinsic rhythm of the atria and a subsequent long RR interval since the ventricles do not depolarize again until the next intrinsic atrial depolarization.

Figure 4:
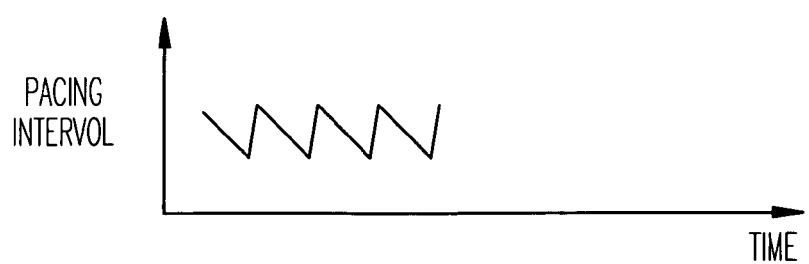
FIG. 4 depicts an exemplary method of overdrive pacing to lengthen the sinus interval.

Another way of restoring RR interval balance is to pace the atria or ventricles at a slowly increasing rate while maintaining the interval ratio near the value of one over a period of time up to a maximum rate limit and then increasing the RR interval to the intrinsic base rate quickly enough to cause a long interval as compared with the short-term average. This saw-tooth variation in the pacing pattern is then repeated at specified intervals. FIG. 4 shows a graph of the pacing interval with respect to time where the pacing interval is gradually decreased over a period of time and then increased to a base value to cause a subsequent long RR interval.

In another embodiment, RR intervals are lengthened by increasing the AV conduction time. This can be implemented by electrical stimulation of the AV node to render it refractory or by stimulation of the parasympathetic nerves innervating the AV node. In the device of FIG. 1A, for example, a stimulation channel may be configured for stimulating parasympathetic nerves. Such autonomic stimulation pulses may be applied to the AV node (or parasympathetic nerves) in form of a single pulse or a pulse train. In another embodiment, both PP and RR intervals may be lengthened by electrical stimulation of the parasympathetic portion of the autonomic nervous system that innervate the SA node.

Either an implantable or an external cardiac device may also be configured to deliver drug therapy upon detection of an increased atrial fibrillation risk. Delivery of anti-arrhythmic or other types of drugs may be delivered by a variety of means including direct injection or transdermal iontophoresis.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac device, comprising:
 a cardiac sensing channel; and
 a controller programmed to measure sinus intervals as the time intervals between successive heart beats during sinus rhythm as detected through the sensing channel;
 wherein the controller is further programmed to assess atrial fibrillation risk by determining the relative frequencies of short and long sinus intervals as compared with an average sinus interval over a specified period of time.

2. The device of claim 1 wherein the controller is programmed to assess atrial fibrillation risk by counting the numbers of short and long sinus intervals over a specified period of time, where a sinus interval is classified as short or long by comparing the sinus interval with a moving average of previous sinus intervals, and wherein an increased risk of atrial fibrillation is determined to exist if the percentage of short sinus intervals is greater than the percentage of long sinus intervals and greater than a specified minimum threshold value.

3. The device of claim 2 wherein a sinus interval is classified as short or long by determining the ratio of the sinus interval to the moving average of previous sinus intervals and then determining if the ratio is within a short interval ratio range or long interval ratio range, respectively.

4. The device of claim 3 wherein the short interval ratio range is between 0.2 and 0.78, and the long interval ratio range is between 1.2 and 2.0.

5. The device of claim 2 wherein the specified minimum threshold value is 0.002.

6. The device of claim 1 wherein the sinus interval is measured as an RR interval measured as the time between ventricular senses.

7. The device of claim 1 wherein the sinus interval is a PP interval measured as the time between atrial senses.

8. The device of claim 1 further comprising a stimulation channel and wherein the controller is further programmed to cause the stimulation channel to deliver an atrial pace following a ventricular sense when the ventricles are refractory to lengthen the RR interval between successive ventricular contractions after detecting an increased risk of atrial fibrillation.

9. The device of claim 1 further comprising a stimulation channel and wherein the controller is further programmed to lengthen the RR interval after detecting an increased risk of atrial fibrillation by causing the stimulation channel to deliver electrical stimulation of the AV node or parasympathetic nerves innervating the AV node.

10. The device of claim 1 further comprising a stimulation channel and wherein the controller is further programmed to lengthen the PP and RR intervals after detecting an increased risk of atrial fibrillation by causing the stimulation channel to deliver electrical stimulation parasympathetic nerves innervating the SA node.

11. The device of claim 1 further comprising a stimulation channel and wherein the controller is further programmed, when an increased risk of atrial fibrillation is detected, to cause the stimulation channel to pace the atria or ventricles at a slowly increasing rate while maintaining an interval ratio near a value of one over a period of time up to a maximum rate limit, and then increase the pacing interval to an intrinsic base rate quickly enough to cause a long RR interval as compared with the short-term average.

12. A method for operating a cardiac device, comprising:
 measuring sinus intervals as the time intervals between successive heart beats during sinus rhythm; and
 assessing atrial fibrillation risk by determining the relative frequencies of short and long sinus intervals as compared with an average sinus interval over a specified period of time.

13. The method of claim 12 further comprising assessing atrial fibrillation risk by counting the numbers of short and long sinus intervals over a specified period of time, where a sinus interval is classified as short or long by comparing the sinus interval with a moving average of previous sinus intervals, and wherein an increased risk of atrial fibrillation is determined to exist if the percentage of short sinus intervals is greater than the percentage of long sinus intervals and greater than a specified minimum threshold value.

14. The method of claim 13 wherein a sinus interval is classified as short or long by determining the ratio of the sinus interval to the moving average of previous sinus intervals and then determining if the ratio is within a short interval ratio range or long interval ratio range, respectively.

15. The method of claim 14 wherein the short interval ratio range is between 0.2 and 0.78, and the long interval ratio range is between 1.2 and 2.0.

16. The method of claim 12 wherein the specified minimum threshold value is 0.002.

17. The method of claim 12 wherein the sinus interval is measured as an RR interval measured as the time between ventricular senses.

18. The method of claim 12 wherein the sinus interval is a PP interval measured as the time between atrial senses.

19. The method of claim 12 further comprising delivering an atrial pace following a ventricular sense when the ventricles are refractory to lengthen the RR interval between successive ventricular contractions after detecting an increased risk of atrial fibrillation.

20. The method of claim 12 further comprising lengthening the RR interval after detecting an increased risk of atrial fibrillation by electrical stimulation of the AV node or parasympathetic nerves innervating the AV node.

21. The method of claim 12 further comprising:
 when an increased risk of atrial fibrillation is detected, pacing the atria or ventricles at a slowly increasing rate while maintaining an interval ratio near a value of one over a period of time up to a maximum rate limit; and
 increasing the pacing interval to an intrinsic base rate quickly enough to cause a long RR interval as compared with the short-term average.

22. The method of claim 12 further comprising lengthening the RR and PP intervals after detecting an increased risk of atrial fibrillation by electrical stimulation of parasympathetic nerves innervating the SA node.

* * * * *

UNITED STATES PATENT AND TRADEMARK OFFICE
CERTIFICATE OF CORRECTION

PATENT NO. : 7,142,912 B2 Page 1 of 1
APPLICATION NO. : 10/194435
DATED : November 28, 2006
INVENTOR(S) : Wagner et al.

It is certified that error appears in the above-identified patent and that said Letters Patent is hereby corrected as shown below:

On Sheet 4 of 4, in Fig. 4, line 2, delete "INTERVOL" and insert -- INTERVAL --, therefor.

Signed and Sealed this

First Day of May, 2007

JON W. DUDAS
*Director of the United States Patent and Trademark Office*